(12) United States Patent
Sangar et al.

(10) Patent No.: US 10,052,617 B2
(45) Date of Patent: Aug. 21, 2018

(54) PRODUCTION OF AROMATICS FROM METHANE

(71) Applicant: ExxonMobil Chemical Patents Inc., Baytown, TX (US)

(72) Inventors: Neeraj Sangar, League City, TX (US); Teng Xu, Houston, TX (US); Larry L. Iaccino, Seabrook, TX (US); Mobae Afeworki, Phillipsburg, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 285 days.

(21) Appl. No.: 14/967,612

(22) Filed: Dec. 14, 2015

(65) Prior Publication Data

US 2016/0096168 A1    Apr. 7, 2016

Related U.S. Application Data

(62) Division of application No. 12/865,773, filed as application No. PCT/US2009/033198 on Feb. 5, 2009, now abandoned.

(60) Provisional application No. 61/030,345, filed on Feb. 21, 2008.

(51) Int. Cl.
| | | |
|---|---|---|
| *C07C 2/76* | (2006.01) | |
| *B01J 29/48* | (2006.01) | |
| *B01J 29/076* | (2006.01) | |
| *B01J 29/90* | (2006.01) | |
| *B01J 35/00* | (2006.01) | |
| *B01J 38/06* | (2006.01) | |

(Continued)

(52) U.S. Cl.
CPC ............ *B01J 29/48* (2013.01); *B01J 29/076* (2013.01); *B01J 29/90* (2013.01); *B01J 35/002* (2013.01); *B01J 38/06* (2013.01);

*B01J 38/14* (2013.01); *C07C 2/76* (2013.01); *C10G 50/00* (2013.01); *B01J 2229/186* (2013.01); *B01J 2229/36* (2013.01); *B01J 2229/40* (2013.01); *C07C 2529/48* (2013.01); *C10G 2300/1025* (2013.01); *C10G 2400/30* (2013.01); *Y02P 20/584* (2015.11); *Y02P 20/588* (2015.11)

(58) Field of Classification Search
CPC ........................................................ C07C 2/76
USPC ................................ 585/415, 417, 418, 420
See application file for complete search history.

(56) References Cited

U.S. PATENT DOCUMENTS

| | | | |
|---|---|---|---|
| 4,016,218 A | 4/1977 | Haag et al. | |
| 4,072,731 A | 2/1978 | Rausch | |
| 4,297,243 A | 10/1981 | Moorehead | |

(Continued)

FOREIGN PATENT DOCUMENTS

| | | |
|---|---|---|
| WO | 2006/068800 A | 6/2006 |
| WO | WO 2006/068814 | 6/2006 |
| WO | 2006/083409 A | 8/2006 |

OTHER PUBLICATIONS

Erena et al., "Study of Physical Mixtures of Cr2O3—ZnO and ZSM-5 Catalysts for the Transformation of Syngas into Liquid Hydrocarbons", Ind. Eng. Chem. Res., vol. 37, Issue 4, pp. 1211-1219, 1998.

(Continued)

*Primary Examiner* — Thuan D Dang
(74) *Attorney, Agent, or Firm* — Priya Prasad

(57) ABSTRACT

A catalyst for the conversion of methane to higher hydrocarbons including aromatic hydrocarbons comprises molybdenum or a compound thereof dispersed on an aluminosili- (Continued)

cate zeolite, wherein the amount of aluminum present as aluminum molybdate in the catalyst is less than 2700 ppm by weight.

6 Claims, 13 Drawing Sheets

(51) Int. Cl.
*B01J 38/14* (2006.01)
*C10G 50/00* (2006.01)

(56) References Cited

U.S. PATENT DOCUMENTS

| | | | |
|---|---|---|---|
| 4,388,224 | A | 6/1983 | Moorehead |
| 4,455,394 | A | 6/1984 | Pinto |
| 4,457,251 | A | 7/1984 | Weman et al. |
| 4,565,803 | A | 1/1986 | Schoenthal et al. |
| 4,666,945 | A | 5/1987 | Osugi et al. |
| 4,678,861 | A | 7/1987 | Mitsui et al. |
| 4,727,206 | A | 2/1988 | Clayson et al. |
| 4,734,536 | A | 3/1988 | Nagahara et al. |
| 4,795,847 | A | 1/1989 | Weitkamp et al. |
| 5,001,295 | A | 3/1991 | Angevine et al. |
| 5,026,937 | A | 6/1991 | Bricker |
| 5,045,520 | A | 9/1991 | Curry-Hyde et al. |
| 5,254,520 | A | 10/1993 | Sofianos |
| 5,336,825 | A | 8/1994 | Choudhary et al. |
| 5,348,982 | A | 9/1994 | Herbolzheimer et al. |
| 5,385,949 | A | 1/1995 | Tierney et al. |
| 5,430,210 | A | 7/1995 | Grasselli et al. |
| 5,527,979 | A | 6/1996 | Agaskar et al. |
| 5,545,674 | A | 8/1996 | Behrmann et al. |
| 5,610,202 | A | 3/1997 | Marchionna et al. |
| 5,656,761 | A | 8/1997 | Nagahara et al. |
| 5,767,039 | A | 6/1998 | Yamagishi et al. |
| 5,969,202 | A | 10/1999 | Ashida et al. |
| 5,973,218 | A | 10/1999 | Ashida et al. |
| 6,037,294 | A | 3/2000 | Drake et al. |
| 6,054,497 | A | 4/2000 | Sofianos et al. |
| 6,114,268 | A | 9/2000 | Wu et al. |
| 6,114,279 | A | 9/2000 | Fukui et al. |
| 6,235,944 | B1 | 5/2001 | Yao et al. |
| 6,239,057 | B1 | 5/2001 | Ichikawa et al. |
| 6,420,295 | B1 | 7/2002 | Bull et al. |
| 6,426,442 | B1 | 7/2002 | Ichikawa et al. |
| 6,504,272 | B2 | 1/2003 | Sakamoto |
| 6,617,275 | B1 | 9/2003 | Sharma et al. |
| 2004/0152586 | A1 | 8/2004 | Ou et al. |
| 2009/0030253 | A1 | 1/2009 | Xu et al. |

OTHER PUBLICATIONS

Cory, D.G. et al., "Suppression of Signals from the Probe in Bloch Decay Spectra", Journal of Magnetic Resonance, vol. 80, Issue 1, pp. 128-132, 1988.
Xu, Teng et al., "The development and applications of CAVERN methods for in situ NMR studies of reaction on solid acids", Topics in Catalysis, vol. 4, Issue 1-2, pp. 109-118, 1997.
Ma et al., "Mo/HMCM-22 Catalysts for Methane Dehydroaromatization: A Multinuclear MAS NMR Study", J. Phys. Chem. B, vol. 105, Issue 9, pp. 1786-1793, 2001.
Borry, Richard W. et al., "*Structure and Density of Mo and Acid Sites in Mo-Exchanged H-ZSM5 Catalysts for Nonoxidative Methane Conversion*", The Journal of Physical Chemistry B, vol. 103, No. 28, pp. 5787-5796 (1999).
Kentgens, A.P.M., "*A Practical Guide to Solid-State NMR of Half-Integer Quadrupolar Nuclei With Some Applications to Disordered Systems*", GEODERMA, vol. 80, pp. 271-306 (1997).
Kraus, H. et al., "*A $^{27}Al$ MQMAS and Off-Resonance Nutation NMR Investigation of Mo-P/$\gamma$-Al$_2$O$_3$ Hydrotreating Catalyst Precursors*", Journal of Physical Chemistry, vol. 100, pp. 16336-16345, (1996).
Massiot, D. et al., "*Modelling One- and Two-Dimensional Solid-State NMR Spectra+*", Magnetic Resonance in Chemistry, vol. 40, pp. 70-76 (2002).
Li, Xiujie et al., "*Olefin Metathesis Over Heterogeneous Catalysts: Interfacial Interaction Between Mo Species and Hβ-Al0 Composite Support*", Journal of Physical Chemistry B, vol. 112, No. 15, pp. 5955-5960 (2008).
Liu, Shenglin et al., "*Promotional Role of Water Added to Methane Feed on Catalytic Performance in the Methane Dehydroaromatization Reaction on Mo/HZSM-5 Catalyst*", vol. 220, pp. 57-65, (2003).
Liu, W. et al., "*Methane Dehydrogenation and Aromatization in the Absence of Oxygen on Mo/HZSM-5: A Study on the Interaction Between Mo species and HZSM-5 by Using $^{27}Al$ and $^{29}Si$ MAS NMR*", Journal of Molecular Catalysis A: Chemical, vol. 120, pp. 257-265 (1997).
Van Bokhoven, J.A. et al., "*Changes in Structural and Electronic Properties of the Zeolite Framework Induced by Extraframework Al and La in H-USY and La(x)NaY: A $^{29}Si$ and $^{27}Al$ MAS NMR and $^{27}Al$ MQ MAS NMR Study*", Journal of Physical Chemistry B, vol. 104, pp. 6743-6754 (2000).
Wang, Hongxia et al., "*Post-steam-treatment of Mo/HZSM-5 Catalysts: An Alternative and Effective Approach for Enhancing Their Catalytic Performances of Methane Dehydroaromatization*", Journal of Physical Chemistry B, vol. 107, pp. 12964-12972 (2003).
Zhang, Jun-Zhong et al., "*Molybdenum ZSM-5 Zeolite Catalysts for the Conversion of Methane to Benzene*", Catalysis Today, vol. 44, pp. 293-300 (1998).
Ismagilov et al., "Methane Conversion to Valuable Chemicals over Nanostructured Mo/ZSM-5 Catalysts", Petroleum Chemistry, vol. 51, No. 3, pp. 174-186, 2011.

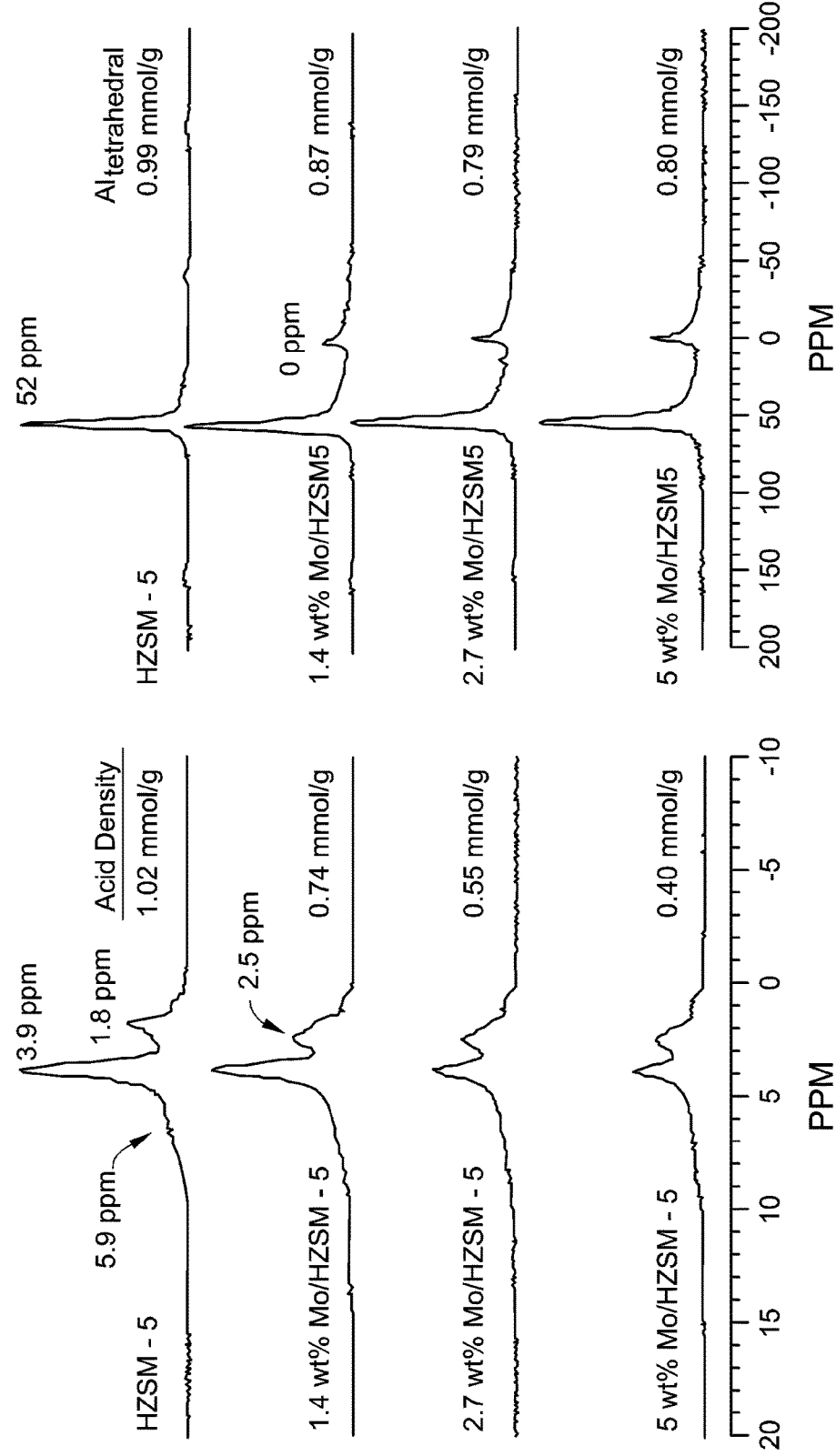

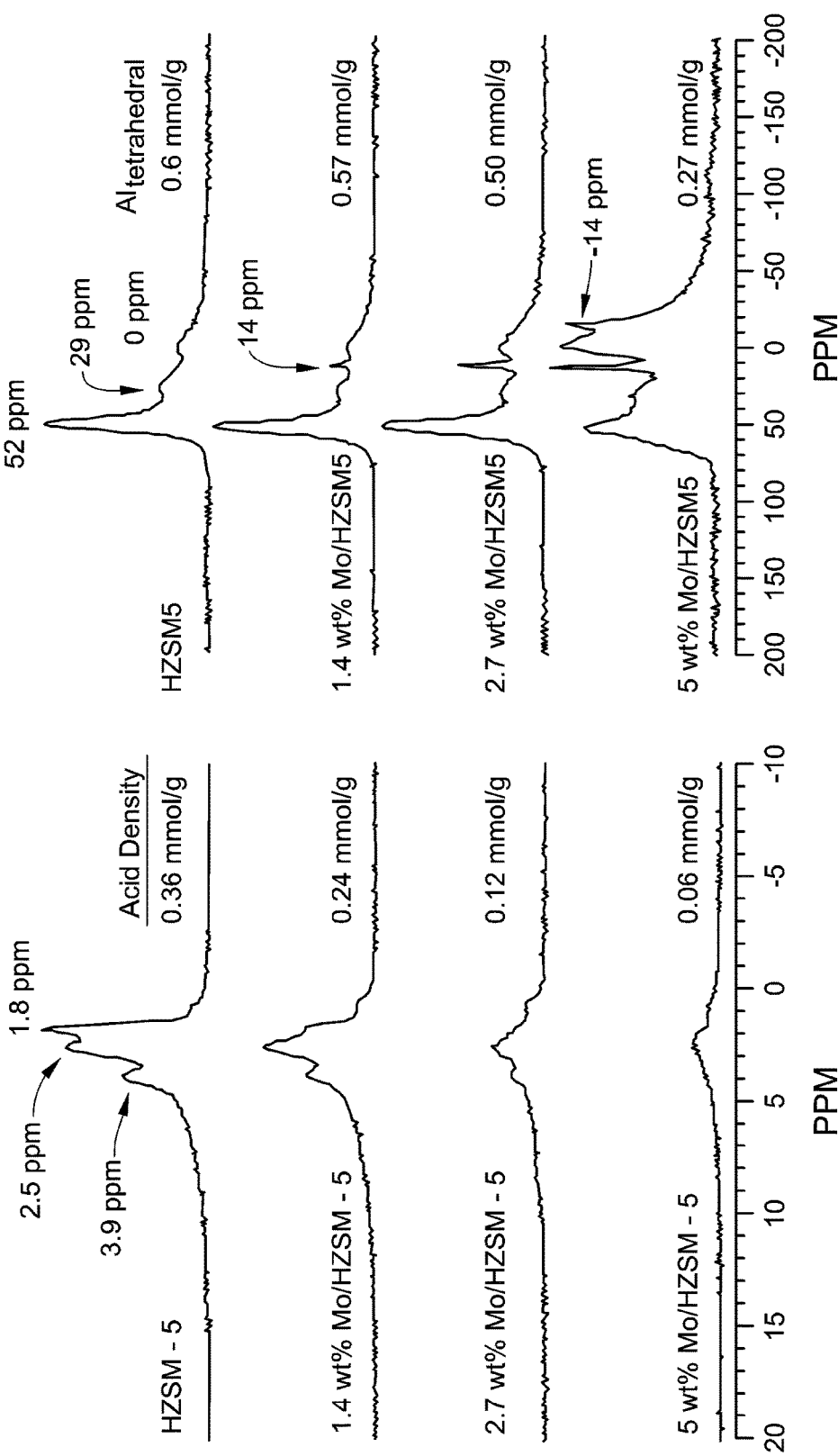

PRODUCTION OF AROMATICS FROM METHANE

CROSS REFERENCE TO RELATED APPLICATIONS

This application is a divisional of U.S. Ser. No. 12/865,773, filed Oct. 14, 2010, which is a 371 National Stage Application of International Application No. PCT/US2009/033198 filed Feb. 5, 2009, which claims the benefit of and priority to U.S. Patent Application No. 61/030,345 filed Feb. 21, 2008, the disclosures of which are incorporated herein by reference in their entireties.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal supported on a zeolite, such as ZSM-5, at high temperature, such as 600° C. to 1000° C.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mol % hydrogen and 50 mol % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

Further in our International Patent Publication No. WO 2006/068814, published Jun. 29, 2006, we have described a process for converting methane to higher hydrocarbons including aromatic hydrocarbons, the process comprising contacting a feed containing methane with a dehydrocyclization catalyst, conveniently molybdenum, tungsten and/or rhenium or a compound thereof on ZSM-5 or an aluminum oxide, under conditions effective to convert said methane to aromatic hydrocarbons and produce a first effluent stream comprising aromatic hydrocarbons and hydrogen, wherein said first effluent stream comprises at least 5 wt % more aromatic rings than said feed; and reacting at least part of the hydrogen from said first effluent stream with an oxygen-containing species to produce a second effluent stream having a reduced hydrogen content compared with said first effluent stream.

However, the successful application of reductive coupling to produce aromatics on a commercial scale requires the solution of a number of serious technical challenges. For example, the reductive coupling process is both endothermic and thermodynamically limited. Thus the cooling effect caused by the reaction lowers the reaction temperature sufficiently to greatly reduce the reaction rate and total thermodynamic conversion if significant make-up heat is not provided to the process.

In addition, the process tends to produce carbon and other non-volatile materials, collectively referred to as "coke", that accumulate on the catalyst resulting in reduced activity and potentially undesirable selectivity shifts, as well as loss of valuable feedstock. Although the coke can be removed from the catalyst by oxidative or reductive regeneration, this leads to lost production time as well as potential damage to the catalyst. There is therefore interest in developing dehydrocyclization catalysts that exhibit reduced coke selectivity without loss in selectivity to the desired aromatic products.

One particularly active catalyst for the dehydroaromatization of methane is molybdenum on an aluminosilicate zeolite, such as ZSM-5, particularly where the molybdenum is highly dispersed and anchored at Bronsted acid sites in the pores of the zeolite. Since the Bronsted acid sites are generated by the aluminum in the zeolite framework, a low zeolite silica/alumina molar ratio is important in determining the effectiveness of the dispersion and anchoring of the molybdenum on the zeolite. However, although the presence of aluminum in the zeolite framework is crucial in producing a highly active dehydroaromatization catalyst, it has now been found that, under certain conditions, the molybdenum and aluminum can interact to produce bulk (that is not anchored to zeolite Bronsted acid sites) aluminum molybdate which can have a detrimental impact on the performance of the catalyst. Thus, bulk aluminum molybdate is found to be highly active for methane conversion with essentially 100% conversion to coke. The present invention therefore seeks to provide a catalyst and process for conversion of methane to aromatics in which the formation of aluminum molybdate during production and use of the catalyst is minimized.

SUMMARY

In one aspect, the invention resides a catalyst for the conversion of methane to higher hydrocarbons including aromatic hydrocarbons, the catalyst comprising molybdenum or a compound thereof dispersed on an aluminosilicate zeolite, wherein the amount of aluminum present as aluminum molybdate in said catalyst is less than 2700 ppm by weight.

In a further aspect, the invention resides a catalyst for the conversion of methane to higher hydrocarbons including aromatic hydrocarbons, the catalyst comprising molybdenum or a compound thereof dispersed on an aluminosilicate zeolite, wherein the amount of hexavalent molybdenum in said catalyst is less than 1.4 wt % by weight.

Conveniently, the amount of molybdenum or said compound thereof in the catalyst is between about 0.1 and about 20% by weight of the catalyst based on elemental molybdenum.

Conveniently, the aluminosilicate zeolite has a silica to alumina mole ratio between about 14 and about 500. In one embodiment, the aluminosilicate zeolite has a Constraint Index between about 1 and about 12, and typically is ZSM-5.

Conveniently, the catalyst has not been exposed to an oxygen-containing gas at a temperature in excess of 650° C.

In yet a further aspect, the invention resides in a process for converting methane to higher hydrocarbons including aromatic hydrocarbons, the process comprising contacting a feed comprising methane with a dehydrocyclization catalyst in a reaction zone under conditions effective to convert said methane to aromatic hydrocarbons, said dehydrocyclization catalyst comprising molybdenum or a compound thereof dispersed on an aluminosilicate zeolite and the amount of aluminum present as aluminum molybdate in said catalyst being less than 2700 ppm by weight.

Conveniently, the dehydrocyclization catalyst, as supplied to said reaction zone, contains less than 2700 ppm by weight aluminum present as aluminum molybdate.

Conveniently, the process is operated so as to maintain the amount of aluminum present as aluminum molybdate in said catalyst at less than 2700 ppm by weight.

In still a further aspect, the invention resides in a process for reducing the coke selectivity of a molybdenum-containing aluminosilicate zeolite catalyst, the process comprising:

(a) providing a catalyst comprising molybdenum or a compound thereof dispersed on an aluminosilicate zeolite wherein the catalyst also comprises aluminum molybdate; and (b) contacting said catalyst with an atmosphere containing steam at a temperature of about 200° C. to about 450° C. and a pressure of at least 1000 kPa to reduce the amount of aluminum molybdate in said catalyst.

BRIEF DESCRIPTION OF THE DRAWINGS

FIGS. 8(a) and 8(b) are $^1$H and $^{27}$Al NMR spectra, respectively, of the Mo/ZSM-5 catalysts of Example 4 after calcination at 500° C.

FIGS. 9(a) and 9(b) are $^1$H and $^{27}$Al NMR spectra, respectively, of the Mo/ZSM-5 catalysts of Example 4 after calcination at 700° C.

for the 1.4 wt % Mo/ZSM-5 catalyst of Example 4 after calcination at 500° C. and after calcination at 700° C.

Figure 11A:
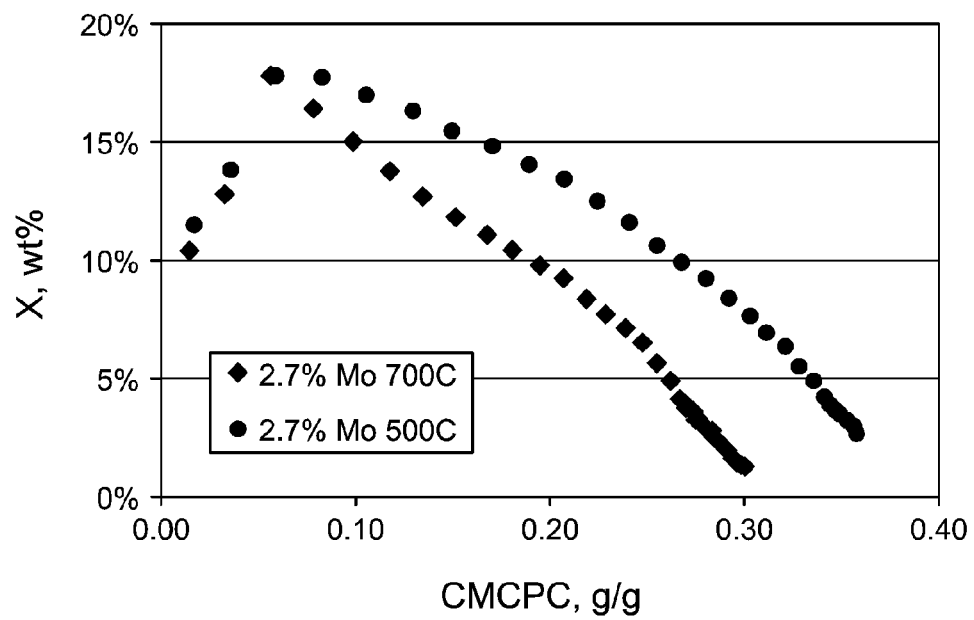
Figure 11B:
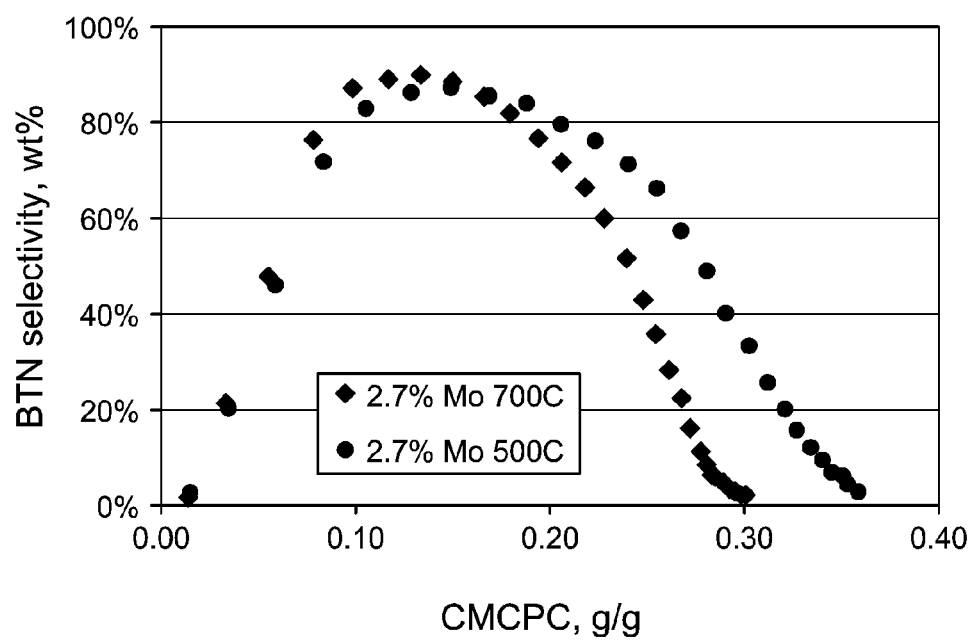

FIGS. 11(a) and 11(b) are graphs comparing the wt % methane conversion (X) and wt % BTN (benzene+toluene+naphthalene) selectivity, respectively, against cumulative grams of methane converted per gram of catalyst (CMCPC) for the 2.7 wt % Mo/ZSM-5 catalyst of Example 4 after calcination at 500° C. and after calcination at 700° C.

Figure 12A:
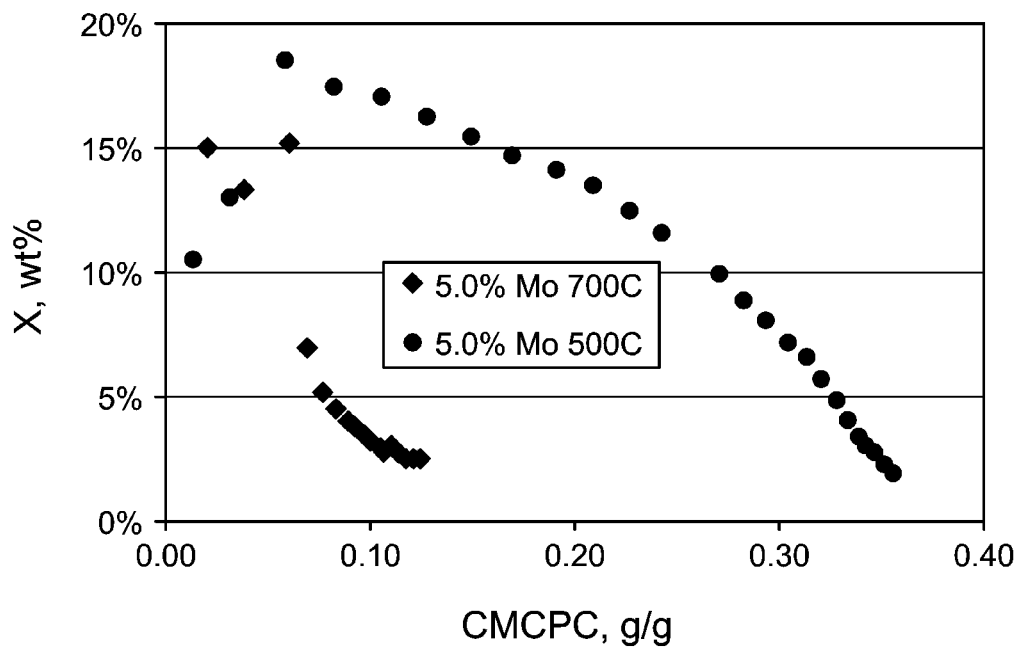
Figure 12B:
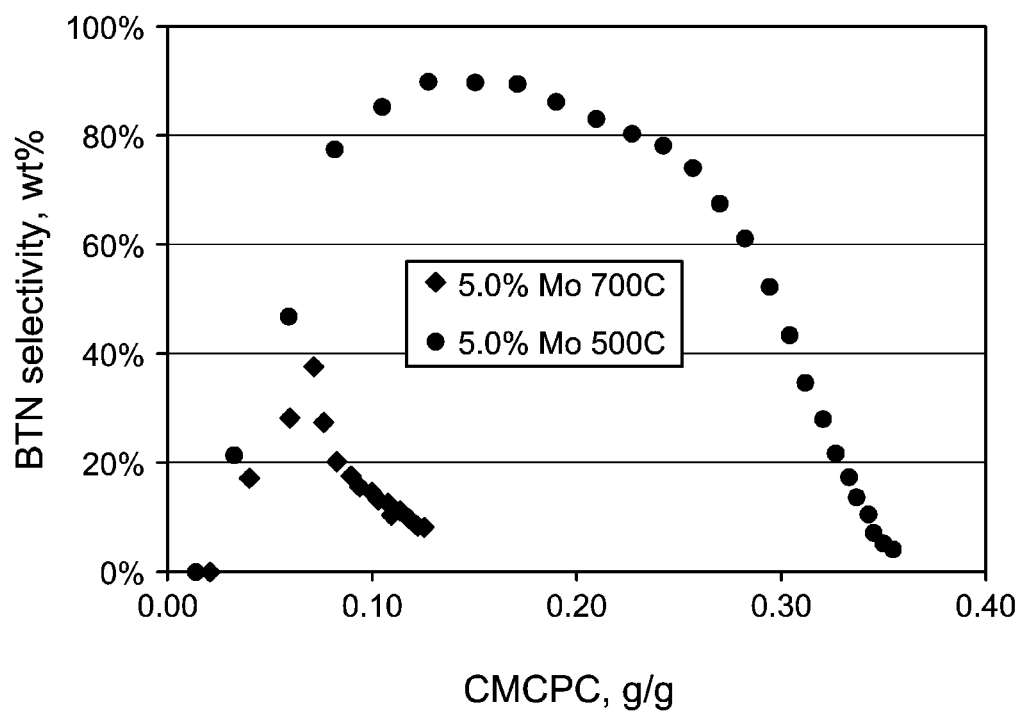

FIGS. 12(a) and 12(b) are graphs comparing the wt % methane conversion (X) and wt % BTN (benzene+toluene+naphthalene) selectivity, respectively, against cumulative grams of methane converted per gram of catalyst (CMCPC) for the 5.0 wt % Mo/ZSM-5 catalyst of Example 4 after calcination at 500° C. and after calcination at 700° C.

Figure 13:
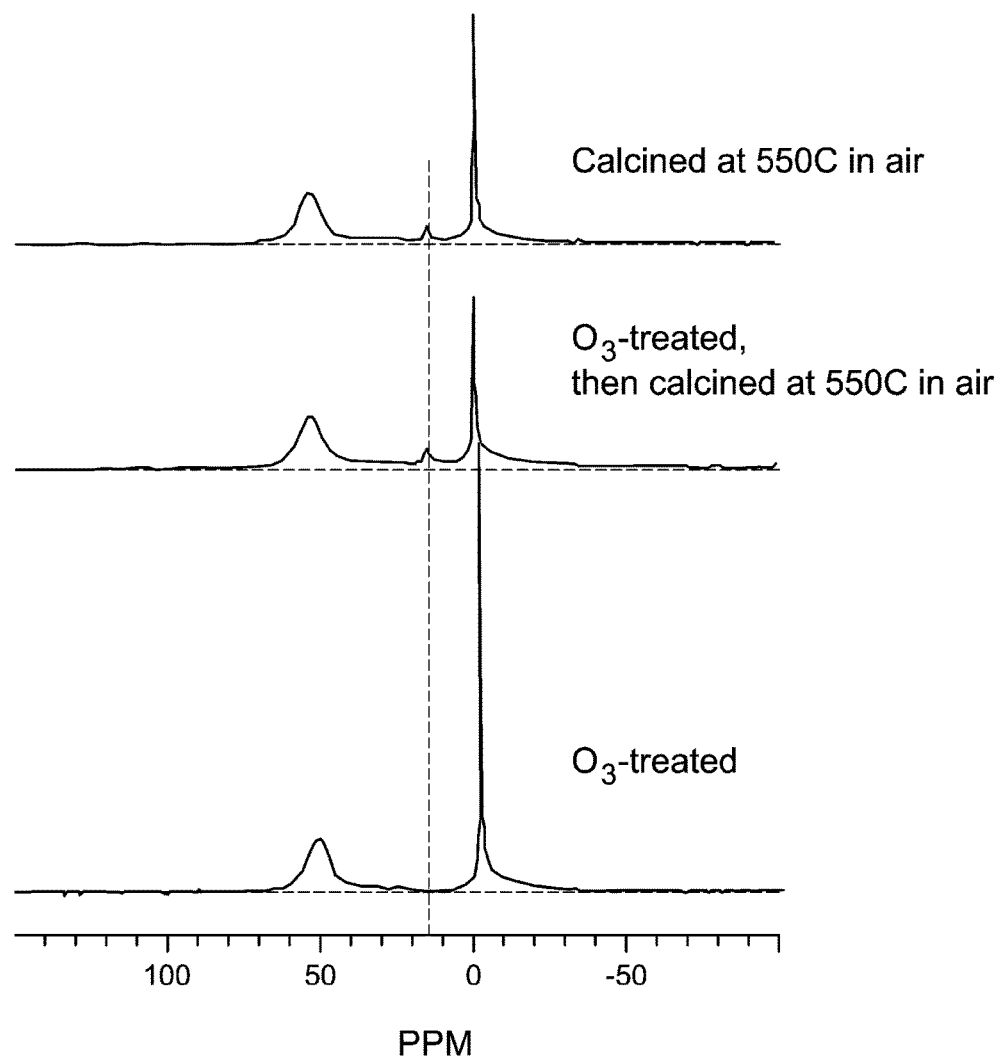

FIG. 13 shows $^{27}$Al NMR spectra of a coked 4.1% Mo/ZSM-5 sample after ozone treatment, and calcination at 550° C. with or without ozone treatment, respectively, as described in Example 5.

DETAILED DESCRIPTION OF THE EMBODIMENTS

As used herein the term "higher hydrocarbon(s)" means hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) comprising at least one carbon atom and at least one non-hydrogen atom, e.g., methanol, ethanol, methylamine, and/or ethylamine.

As used herein the term "aromatic hydrocarbon(s)" means molecules containing one or more aromatic rings. Examples of aromatic hydrocarbons are benzene, toluene, xylenes, naphthalene, and methylnaphthalenes.

The terms "coke" and "carbonaceous material" are used herein interchangeably to mean carbon containing materials, which are essentially non-volatile solids at the reaction conditions, with a low hydrogen content relative to carbon content (such as a H/C molar ration of less than 0.8; most probably less than 0.5). These may include crystalline graphite, graphitic sheets, graphitic fragments, amorphous carbon, or other carbon containing structures which are essentially non-volatile solids at the reaction conditions.

The present invention provides a catalyst and process for the conversion of methane to higher hydrocarbons including aromatic hydrocarbons, wherein the catalyst comprises molybdenum or a compound thereof dispersed on an aluminosilicate zeolite and wherein the amount of aluminum present as aluminum molybdate in said catalyst is less than 2700 ppm by weight and/or hexavalent molybdenum in said catalyst is less than 1.4% by weight. The presence of aluminum in the form of aluminum molybdate can be detected via Al-NMR and its presence is found to be correlated with a deterioration in selectivity and yield of aromatic hydrocarbons and an increase in the production of coke. The amount of aluminum molybdate and/or hexavalent molybdenum can be controlled at the desired low level by effecting at least one of steps of (i) controlling the conditions of catalyst manufacture to minimize interaction between aluminum and molybdenum, (ii) steaming the catalyst to convert bulk aluminum molybdate to MoOx species and redisperse these species on the Bronsted acid sites of the zeolite, and (iii) controlling the conditions of catalyst activation, reaction and regeneration to minimize interaction between aluminum and molybdenum.

The conversion of methane to aromatics generates hydrogen as a by-product and hence the present process also includes one or more hydrogen rejection steps in which at least part of the hydrogen by-product is converted to higher value products.

Feedstock

Any methane-containing feedstock can be used in the present process but in general the process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can be converted directly to aromatics products in the dehydrocyclization step. In addition, as will be discussed below, carbon dioxide can be converted to useful aromatics products either directly in the dehydrocyclization step or indirectly through conversion to methane and/or ethane in a hydrogen rejection step.

Nitrogen and/or sulfur impurities are also typically present in methane-containing streams and desirably are removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from a hydrogen rejection step, added as separate co-feeds or can be present in the methane stream, such as, for example, when ethane is present in a natural gas feed. Higher hydrocarbons recycled from a hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization Catalyst

The dehydrocyclization catalyst employed herein comprises molybdenum or a compound thereof, such as molybdenum carbide, dispersed on an aluminosilicate zeolite. Conveniently, the molybdenum or compound thereof is present in an amount between about 0.1% and about 20%, such as between about 1% and about 10%, for example between 1% and 5%, based on elemental Mo by weight of the total catalyst. However, In addition to molybdenum and the zeolite support, the catalyst can contain one or more other dehydrogenation metals, such as tungsten, zinc, and/or rhenium.

Suitable aluminosilicate zeolites for use in the dehydrocyclization catalyst include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), and VFI (e.g., VPI-5), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Generally, the aluminosilicate zeolite employed herein has a Constraint Index between about 1 and about 12 (as defined in U.S. Pat. No. 4,016,218, which is incorporated herein by reference) and typically is ZSM-5. Conveniently, the aluminosilicate zeolite has a silica to alumina mole ratio between about 14 and about 500, such as between about 20 and about 300, for example between about 22 and about 280.

The catalyst may also include a binder to provide the catalyst particles with the requisite size, density and hardness for use in the dehydroaromatization process. Suitable binders include refractory inorganic oxides such as alumina, silica, amorphous silica-alumina, zirconia, titanium oxide, and boron oxide.

The molybdenum component can be dispersed on the zeolite support by any means well known in the art such as co-precipitation, incipient wetness, evaporation, impregnation, spray-drying, sol-gel, ion-exchange, chemical vapor deposition, diffusion and physical mixing. In addition, the zeolite support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to the internal pore structure of the support.

Irrespective of how the molybdenum component is applied to the zeolite support and/or how the support is treated to modify its properties, in embodiments it is generally important to avoid exposure of the molybdenum containing catalyst to an oxygen-containing gas at a temperature in excess of 650° C., preferably 600° C., more preferably 550° C., still more preferably 500° C. As used herein, the term "oxygen-containing gas" means a gas containing $O_2$ and/or $O_3$ (molecular oxygen and/or ozone). From a practical viewpoint, it is preferred that the limit of exposure of the molybdenum containing catalyst be no greater than 100 wt ppm, preferably 10 wt ppm, still more preferably 1 wt ppm, of molecular oxygen, ozone, or the combination thereof in a gas mixture. Thus, it has now been found that in a high temperature oxidizing environment the molybdenum can react with aluminum (typical present in it's oxide form) present in the zeolite or the binder to produce bulk (that is not anchored to zeolite Bronsted acid sites) aluminum molybdate. Moreover, it is found that this bulk aluminum molybdate can have a detrimental impact on the performance of the catalyst by increasing its coke selectivity. For example, where the molybdenum component is deposited on the zeolite support by impregnation of the support with a solution of a molybdenum compound, such as an ammonium heptamolybdate solution, it will normally be necessary to subject the catalyst to a calcination step to convert the molybdenum compound the desired elemental or carbide form. If the calcination is conducted in air or other oxygen-containing gas, it is therefore desirable that the calcination temperature is less than or equal to 650° C., for example less than or equal to 550° C. Generally, it is important to maintain the concentration of aluminum present as aluminum molybdate in said catalyst less than 2700 ppm by weight, and/or of hexavalent molybdenum in said catalyst at less than 1.4% by weight.

Dehydrocyclization Process

In the dehydrocyclization step of the present process, the methane containing feedstock is contacted with the particulate dehydrocyclization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4 + 2H_2 \quad \text{(Reaction 1)}$$

$$6CH_4 \leftrightarrow C_6H_6 + 9H_2 \quad \text{(Reaction 2)}$$

$$10CH_4 \leftrightarrow C_{10}H_8 + 16H_2 \quad \text{(Reaction 3)}$$

Carbon dioxide that may be present in the feed improves catalyst activity and stability by facilitating reactions such as:

$$CO_2 + \text{coke} \rightarrow 2CO \quad \text{(Reaction 4)}$$

but negatively impacts equilibrium by allowing competing net reactions, such as;

$$CO_2 + CH_4 \leftrightarrow 2CO + 2H_2 \quad \text{(Reaction 5)}.$$

The dehydrocyclization step is conducted by contacting the methane-containing feedstock with the particulate dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction.

In some embodiments, a non-catalytic particulate material may be supplied to the dehydrocyclization reaction zone(s) in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

Typically, the mass ratio of the flow rate of the catalytic particulate material plus any non-catalytic particulate material over the flow rate of the hydrocarbon feedstock in the or each dehydrocyclization reaction zone is from about 1:1 to about 100:1, such as from about 1:1 to about 40:1, for example from about 5:1 to 20:1.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence in some configurations it is possible to reduce the difference between the maximum and minimum temperatures to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$.

The major components of the effluent from the dehydrocyclization step are hydrogen, benzene, naphthalene, carbon monoxide, ethylene, and unreacted methane. Typically, the effluent contains at least 5 wt. %, such as at least 10 wt. %, for example at least 20 wt. %, conveniently at least 30 wt. %, more aromatic rings than the feed.

The benzene and naphthalene are separated from the dehydrocyclization effluent, for example, by solvent extraction followed by fractionation, and can be recovered as a product stream. However, as will be discussed below, at least part of these aromatic components can be submitted to an alkylation step, before or after product recovery, to produce higher value materials, such as xylenes. Moreover, as will be discussed below, the present process utilizes the hydrogen generated as a by-product of the dehydrocyclization reaction and in particular converts at least part of the hydrogen to higher value products.

Catalyst Regeneration

The dehydrocyclization reaction tends to deposit coke on the catalyst and hence, to maintain the activity of the dehydrocyclization catalyst, at least part of the catalyst is continuously or intermittently regenerated. This is typically achieved by withdrawing a portion of the catalyst from the or each reaction zone, either on an intermittent, or a continuous basis, and then transferring the catalyst portion to a separate regeneration zone. In the regeneration zone, the coked dehydrocyclization catalyst is contacted with a regeneration gas under conditions effective to remove at least a portion of the carbonaceous material on the catalyst. The regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In one embodiment, the regeneration is conducted in the presence of an oxygen-containing gas. Generally, the oxygen-containing gas contains less $O_2$ than air, such as less than 10 wt %, more preferably less than 5 wt %, $O_2$, and is preferably substantially free of $H_2O$. The regeneration gas may also contain $CO_2$ to gasify a portion of the coke from the catalyst. Convenient sources of the regeneration gas are an $O_2$ depleted, $N_2$ enriched stream from an air separation unit and a high $CO_2$ reject stream from industrial or natural gas processing to which air or $O_2$ has been added to achieve the target $O_2$ concentration. Suitable conditions for regeneration with an oxygen-containing gas include a temperature from about 400° C. to about 700° C., such as from about 550° C. to about 650° C., a pressure between 10 and 100 psia (69 and 690 kPa), such as between 15 and 60 psia (103 and 414 kPa), and a catalyst residence time between 0.1 and 100 minutes, such as between 1 and 20 minutes.

It will, however, be appreciated from the foregoing discussion that regeneration in an oxidizing environment can generate bulk aluminum molybdate and hence increase the coke selectivity of the regenerated catalyst. In general, therefore, it is preferable to conduct the regeneration in the presence of a hydrogen-containing gas whereby coke on the catalyst is converted to methane. Generally, the hydrogen-containing gas does not contain significant quantities of methane or other hydrocarbons; typically with the hydrocarbon content being less than 20 mol %, such as less than 10 mol %, for example less than 2 mol %. In one embodiment, the hydrogen required for the regeneration is obtained at least in part from the hydrogen-containing effluent from the dehydrocyclization reaction. Conveniently, hydrogen regeneration conditions comprise a temperature from about 700° C. to about 1200° C., such as from about 800° C. to about 1000° C., such as about 850° C. to about 950° C. and a pressure of at least 100 kPaa, such between about 150 kPaa and about 5000 kPaa.

Generally, the coked dehydrocyclization catalyst removed from the or each reaction zone will be at a lower temperature than the optimum for hydrogen regeneration and hence the removed catalyst is initially heated to the desired regeneration temperature by direct and/or indirect contact with combustion gases produced by combustion of a supplemental source of fuel. The heating is conducted in a heating zone which may be in the same vessel as the regeneration zone or which may be in a separate vessel from the regeneration zone. By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, in the case of direct heat transfer to the dehydrocyclization catalyst, the use of an oxygen-lean atmosphere minimizes the formation of aluminum molybdate as well as inhibiting oxidation of metal carbides present in the catalyst and reducing the average steam partial pressure and hence hydrothermal catalyst aging.

Alternatively, a suitable supplemental fuel source is hydrogen and, in particular, part of the hydrogen generated as a by-product of the aromatization reaction.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, supplying heat to the catalyst and then returning the heated catalyst back to the reaction zone. Where catalyst regeneration is effected in the presence of hydrogen, the preheating of the coked catalyst normally required to bring the catalyst to the optimum regeneration temperature may provide one possible route for supplying heat to the dehydrocyclization reaction.

Alternatively, some or all of the heat required to maintain the dehydrocyclization reaction can be supplied by a separate catalyst reheating step. In this embodiment, part of the catalyst is withdrawn from the reaction zone and is transferred to a separate heating zone, where the catalyst is heated by direct or indirect contact with hot combustion gases generated by burning a supplemental source of fuel. The heated catalyst is then returned to the reaction zone with or without undergoing hydrogen regeneration.

Catalyst Reactivation

As discussed above, when the molybdenum-containing aluminosilicate zeolite catalyst employed in the present dehydrocyclization process is subjected to high temperature oxidizing conditions, such as can occur during catalyst manufacture and regeneration, the molybdenum and aluminum can interact to produce bulk aluminum molybdate, which is highly coke-selective. Although it is preferable to control the conditions to which the catalyst is exposed to avoid aluminum molybdate production, in practice it may be necessary to periodically reactivate the catalyst by converting the aluminum molybdate back to MoOx species and to redisperse the oxide species on the remaining Bronsted acid sites of the zeolite. In this way, the coke selectivity of the catalyst can be reduced.

In one embodiment, catalyst reactivation is achieved by contacting the aluminum molybdate-containing catalyst with an atmosphere containing steam, such as an atmosphere comprising about 1 volume % to about 100 volume % steam, at a temperature of about 200° C. to about 450° C., such as about 250° C. to about 350° C., and a pressure of at least 1000 kPa, such as about 4000 kPa to about 16500 kPa. In this way, the concentration of aluminum present in bulk aluminum molybdate can be reduced from for example, values such as 3500 ppm by weight or higher to less than 1000 ppm by weight.

Catalyst Recarburizing

It will be appreciated that heating the dehydrocyclization catalyst for the purposes of regeneration, reactivation and/or for heat transfer may subject the catalyst to oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated, reactivated and/or reheated catalyst may be transferred to a catalyst treatment zone separate from the regeneration zone, the reactivation zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, $CO$, $H_2$, $H_2O$ and inert diluents. Alternatively, the carburizing gas may be a mixture of hydrogen and at least one of CO and $CO_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Serial No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \qquad \text{(Reaction 6)}$$

$$2CO_2 + 7H_2 \leftrightarrow C_2H_6 + 4H_2O \qquad \text{(Reaction 7)}$$

The carbon dioxide employed is conveniently part of a natural gas stream and typically the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2$:$CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

  (Reaction 8)

and by the following reaction:

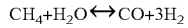

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, for example from about 500 $hr^{-1}$ to about 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of: i) at least one metal from Group 3 and at least one metal from Groups 4-15 of the Periodic Table of the Elements; ii) at least one metal from Groups 5-15 of the Periodic Table of the Elements, and at least one metal from at least one of Groups 1, 2, and 4 of the Periodic Table of the Elements; iii) at least one metal from Groups 1-2, at least one metal from Group 3, and at least one metal from Groups 4-15 of the Periodic Table of the Elements; and iv) two or more metals from Groups 4-15 of the Periodic Table of the Elements; and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

In addition to hydrogen, the other major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more for example about 500 $hr^{-1}$ to about 10,000 $hr^{-1}$.

The effluent from the reverse shift reactor can then be fed to an alkylation reactor operating under conditions to cause reactions such as the following to occur:

$$CO + 2H_2 \leftrightarrow CH_3OH \quad \text{(Reaction 9)}$$

$$CH_3OH + C_6H_6 \rightarrow toluene + H_2O \quad \text{(Reaction 10)}$$

$$2CH_3OH + C_6H_6 \rightarrow xylenes + 2H_2O \quad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

The invention will now be more particularly described with reference to the accompanying drawings and the following non-limiting Examples.

Figure 1:
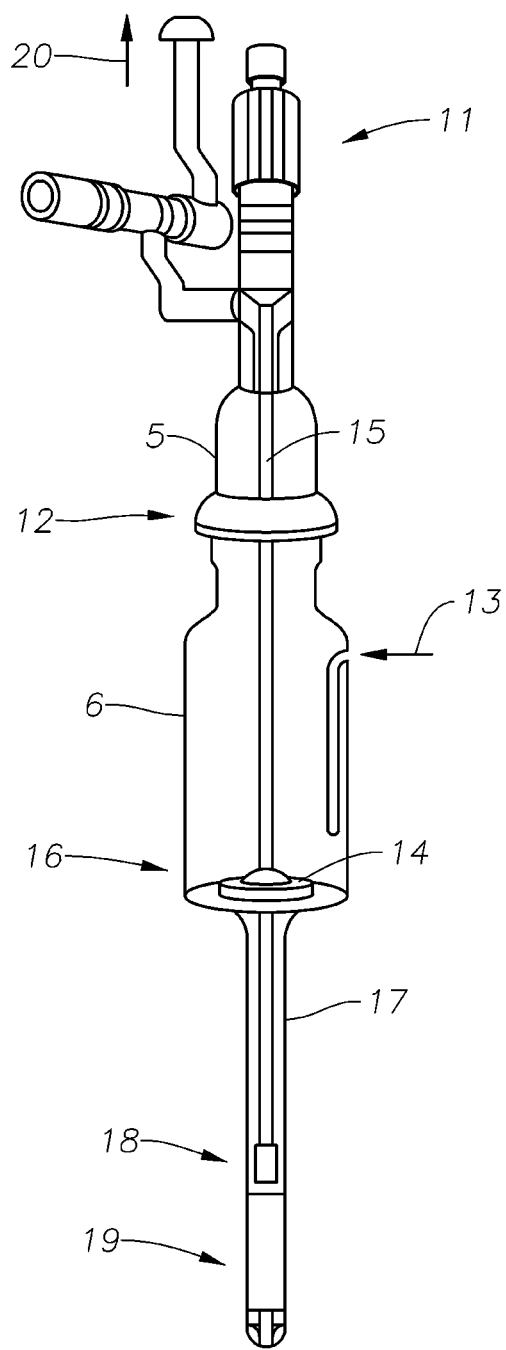
FIG. 1 is a diagram of a device for measuring by NMR the proton density of catalyst samples produced in the Examples.

In the Examples, measurements of the amount of Bronsted acid sites in a catalyst are made using an NMR procedure for determining the proton density of the catalyst. In particular, the catalyst proton density is determined using a shallow bed CAVERN device, as shown in FIG. 1. Thus, referring to FIG. 1, the CAVERN device comprises an upper housing 5 and lower housing 6 connected by a joint 12. The device also includes a mechanism 11 for lifting a glass trapdoor 16 from a catalyst bed 14, a line 20 for connecting the housing 5, 6 to a vacuum pump, and thermocouple 13 for heating a catalyst sample in the bed 14. A 5 mm outside diameter glass tube 17 slides over a 3 mm diameter stainless steel rod 15, and rests between an endcap 18 and the glass trapdoor 16. The stainless steel rod 15 is retracted by turning the mechanism 11, whereby the glass tube 17 raises the glass trapdoor 16 above the catalyst bed 14. By gently turning or shaking the CAVERN device, the catalyst sample (not shown) falls into a Magic Angle Spinning (MAS) rotor 19.

In order to determine the proton density of a catalyst sample, a thin layer of the sample is spread out in the catalyst bed 14 and then any moisture absorbed on the catalyst sample is removed by evacuating the housing 5, 6 and raising the temperature of the catalyst sample to 350° C. via thermocouple 13. The catalyst sample is typically held under vacuum (such as $1\times10^{-5}$ kPa) at 350° C. for 3 hours prior to NMR measurement. The dried catalyst sample is then loaded into a 5 mm NMR rotor, such as MAS rotor 19, and the rotor is sealed with a Kel-F end cap by manipulating the CAVERN device. All the operations are performed while the catalyst sample is still under vacuum, ensuring the sample integrity for NMR study.

$^1$H NMR experiments are performed on a 400 MHz solid state NMR spectrometer operating at 399.8 MHz for $^1$H. The NMR spectrometer used is a Varian Infinity Plus 400 MHz solid state NMR with an Oxford AS400 magnet. Quantitative $^1$H spectra are obtained by the use of rotor-synchronized spin-echo sequence ($\pi/2$-$t_{D1}$-$\pi$-$t_{D2}$-Echo) using 8 to 12 kHz spinning speeds. Typically, 3.5-μs $\pi/2$ pulses, $t_{D1}$ of 125-μs and $t_{D2}$ of 113.1 μs are used for a spinning speed of 9 kHz. Spectra acquired using the solid echo sequence show some background signal, presumably from the spinning module and the endcap 18 of the MAS rotor 19. A solid echo sequence with DEPTH removes the background signal from the spectra. The DEPTH sequence consists of a 90° pulse (3.5-μs) followed by two 180° pulses. A description of the DEPTH sequence appears in Corey, D. G.; Ritchey, W. M. *J. Magn. Reson.* 1988, 80, 128, incorporated herein by reference. A pulse delay of 10 seconds is sufficient for quantifying proton density of the catalyst samples tested. Acetone is used as secondary standard for $^1$H shift (2.1 ppm). All the reported chemical shifts are referenced to tetramethylsilane (TMS) at 0 ppm.

After the desired NMR spectra have been acquired, the weight of MAS rotor 19, the catalyst sample and the endcap 18 are determined followed by weight determination of the rotor and the endcap 18 upon unpacking the catalyst sample. The difference in the two weights is the amount of the catalyst sample in the MAS rotor 19.

Further details regarding the operation of the CAVERN device are disclosed in Xu, T.; Haw, J. F. *Top. Catal.* 1997, 4, 109-118, incorporated herein by reference.

$^{27}$Al Solid state NMR experiments were performed on a 400 MHz solid state NMR spectrometer (Varian) operating at 104.2 MHz for $^{27}$Al. 10 wt % Al(NO$_3$)$_3$ solution (0.0 ppm) was used as the external chemical shift standard for $^{27}$Al. Quantitative $^{27}$Al spectra were acquired using a single pulse sequence with a 10° flip angle (90° pulse=10 μs) and 0.1 s pulse delay. Prior to $^{27}$Al NMR measurement, samples were kept at least overnight in a desiccator filled with saturated ammonia nitrate solution to ensure complete hydration. $^{27}$Al NMR experiments were acquired using Varian 5.0 mm probes spun at 8 to 10 KHz with active spin speed control (±1 Hz). Assignment of $^{27}$Al chemical shifts at about 14 ppm and −14 ppm to hydrated aluminum molybdate and aluminum molybdate, respectively, is disclosed in Ma, D., Shu, Y., Han, X., Xu, Y., and Bao, X., *J. Phys. Chem. B* 2001, 105, 1786-1793, incorporated herein by reference.

The concentration of various $^{27}$Al species was quantified by integrating peak intensity, $I_i$, for individual resonance, where $I_i$ denotes integrated peak intensity for species i. The fraction, $x_i$ of individual species was calculated based on peak intensity of the species ($I_i$) divided by the total intensity ($\Sigma I_i$ or sum of peak intensity for all the species) from the $^{27}$Al spectrum. The concentration of Al species (mmol/g) in the catalyst sample was quantified by multiplying $x_i$ with Al concentration (mmol/g) in the sample determined by elemental analysis in separate experiments. Al concentration in a sample measured from elemental analysis, such as ICP, gives the total concentration of Al in the sample.

EXAMPLE 1

Four bulk Mo and Al mixed oxide catalysts were prepared via co-precipitation of their corresponding salt solutions using ammonium hydroxide as the precipitating agent. First, solution A is prepared by dissolving stoichiometric amount of aluminum nitrate monohydrate in distilled water at concentration of about 0.4 gram of aluminum salt per gram of solution. Solution B containing stoichiometric amount of ammonium molybdate tetrahydrate is dissolved in distilled water at concentration ranging from 0.04 to 0.30 gram of molybdenum salt per gram of solution. Ammonium hydroxide solution (30% NH$_3$) is then added to solution B (about 3 g of ammonium hydroxide solution for 1 g of solution B). Solution B is then slowly added drop wise to solution A while stirring solution A. After addition of solution B is complete, an additional ammonium hydroxide solution is added to the suspension to reach gelation point. The resultant gel is transferred to an alumina crucible and dried in vacuum oven at 75° C. for 2 hours. The dried gel is transferred to a calcination oven and further heated to 150° C. for 2 hours and then to 600° C. for 4 hours. The molybdenum loading (wt % metal basis) was varied by changing the amount of ammonium molybdate tetrahydrate in solution B. Catalysts containing 2.5 wt %, 5 wt %, 10 wt % and 20 wt % Mo were prepared.

Figure 2A:
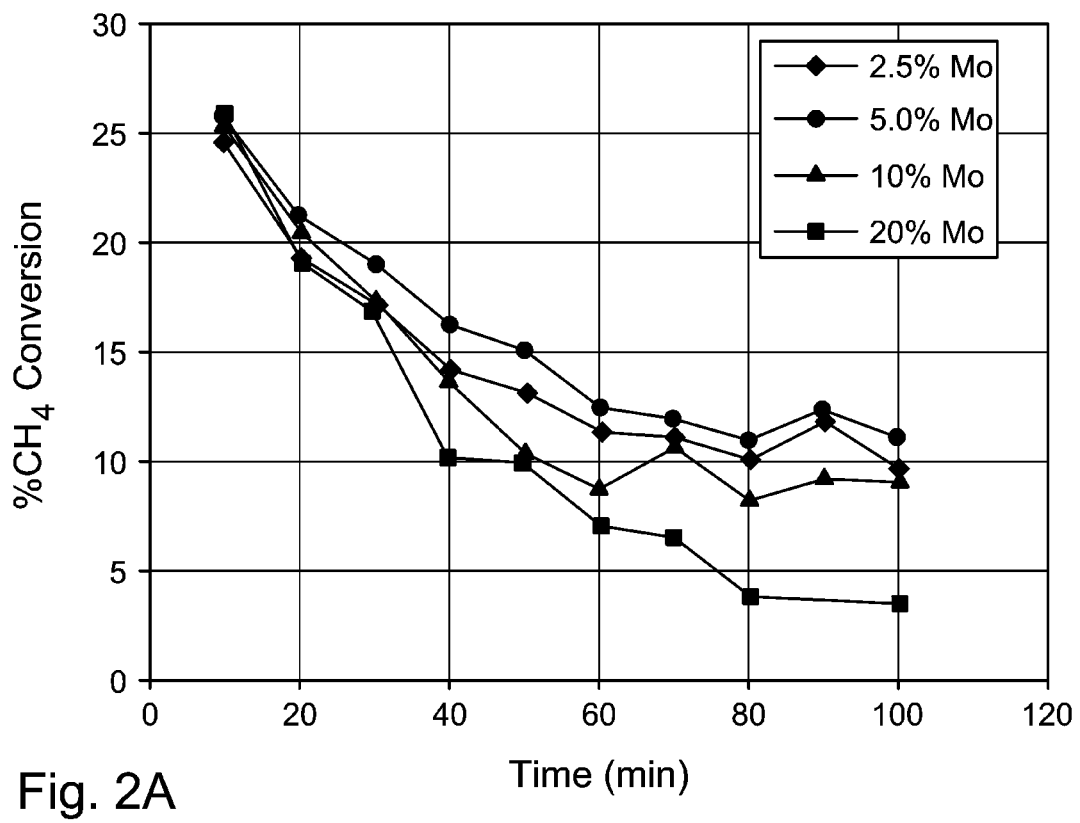
FIGS. 2(a) and 2(b) are graphs of % methane conversion and % benzene selectivity (carbon basis), respectively, against time for the dehydrocyclization of methane according to the process of Example 1 and using molybdenum and aluminum mixed oxide catalyst containing varying amounts of molybdenum.
Figure 2B:
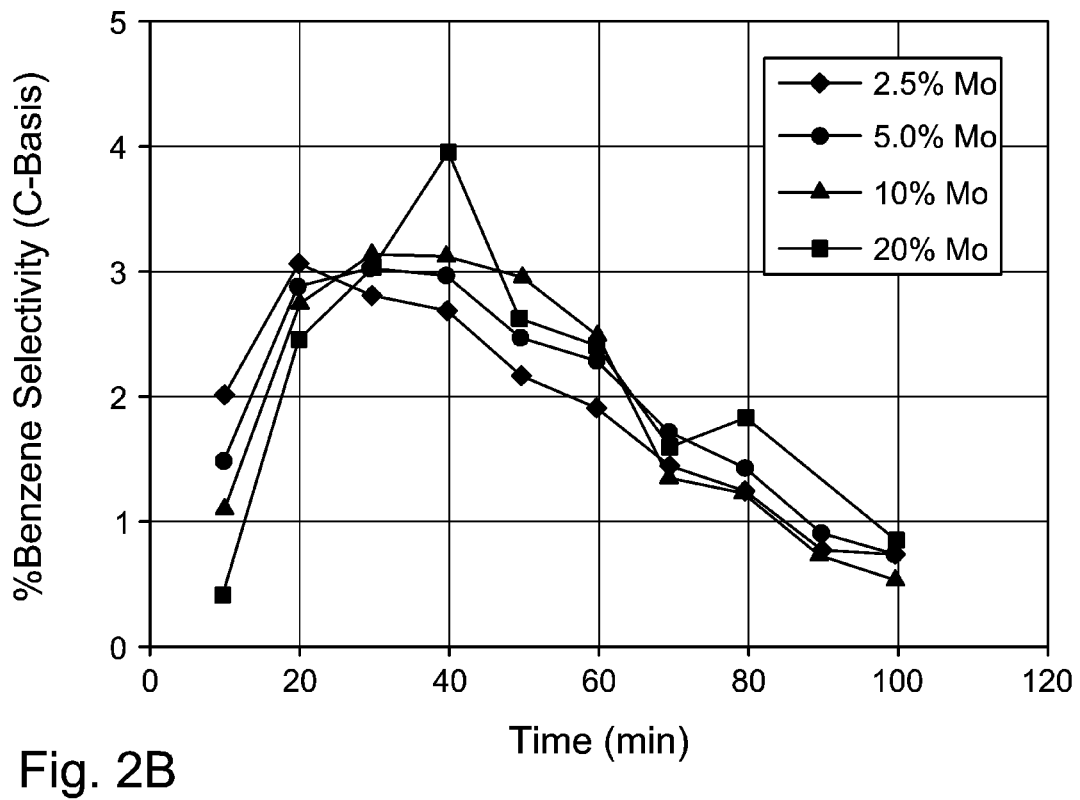

The performance of resultant bulk Mo—Al mixed oxide catalysts was measured at 800° C. using feed comprising 95 vol % CH$_4$ and 5 vol % Ar at a WHSV (respect to methane) of 2 hr$^{-1}$. The results are shown in FIGS. 2(*a*) and 2(*b*) and show that, although these materials are very active for methane conversion, the selectivity for benzene formation is <5%. In addition, these materials are significantly more active than bulk Mo$_2$C which shows a methane conversion of about 10% at 900° C. using the same feed at a WHSV (respect to methane) of 1 hr$^{-1}$.

EXAMPLE 2

A ZSM-5 catalyst comprising 2.7 wt % Mo was prepared by impregnation of a ammonium heptamolybdate solution onto a NH$_4^+$-ZSM-5 support (having a Si/Al$_2$ ratio of 25) via incipient wetness, followed by drying at 120° C. for 2 hours and final calcination at 500° C. for 6 hours in flowing air. Samples of the catalyst were subjected to different aging treatments involving exposing the catalyst to cyclic carburization (performed by ramping from 600 to 850° C. at 10° C./min using 95% CH$_4$—Ar feed at WHSV of 1.6 hr$^{-1}$) and regeneration (performed at 600° C. using 4% O$_2$ for 45 min), with the number of cycles being varied between 0 (no aging), 2, 5, 11 and 33.

Figure 3:
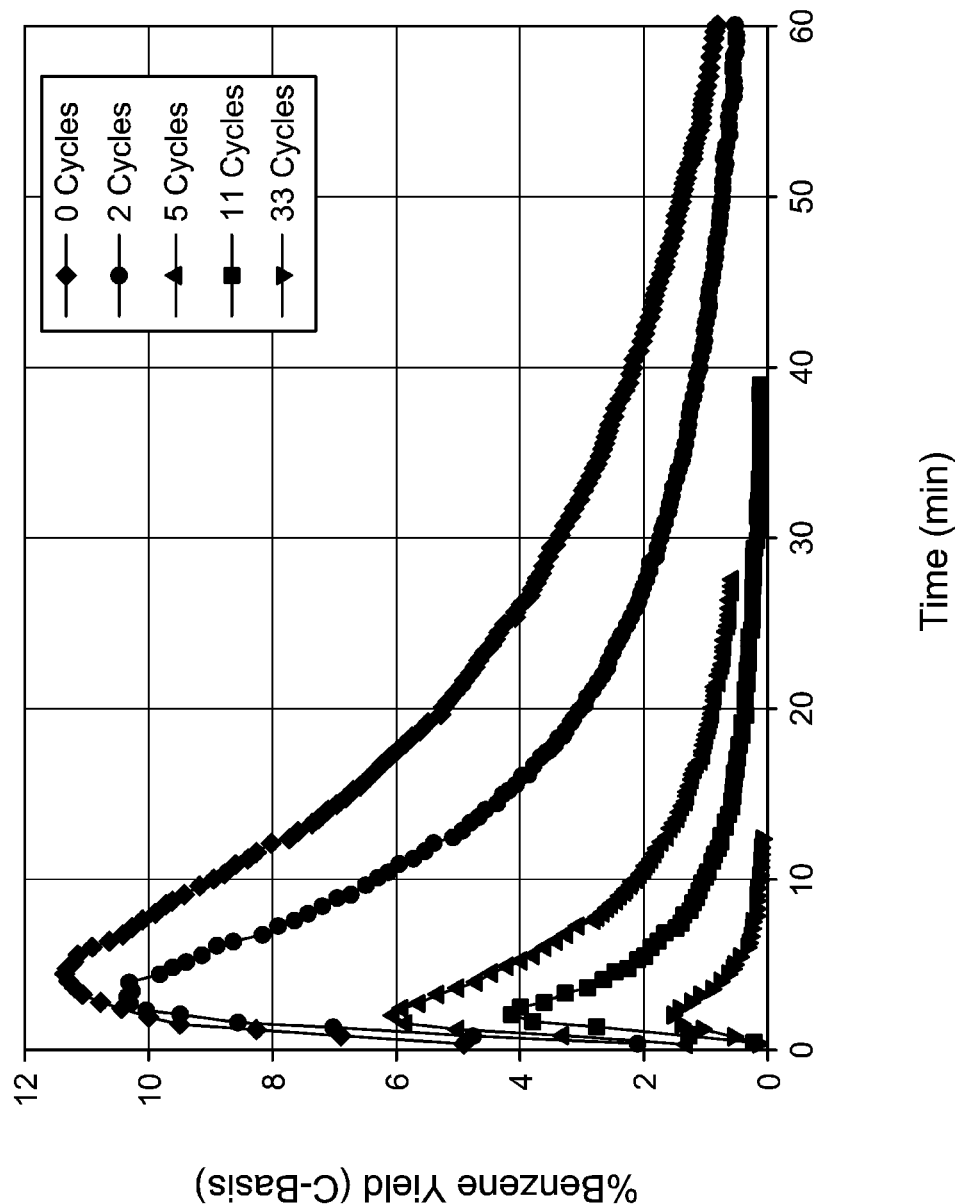
FIG. 3 is a graph of % benzene yield (carbon basis) against time for the dehydrocyclization of methane according to the process of Example 2 and using as a catalyst ZSM-5 containing 2.7 wt % molybdenum after the catalyst has undergone a varying number of carburization/oxidative regeneration cycles.
Figure 4A:
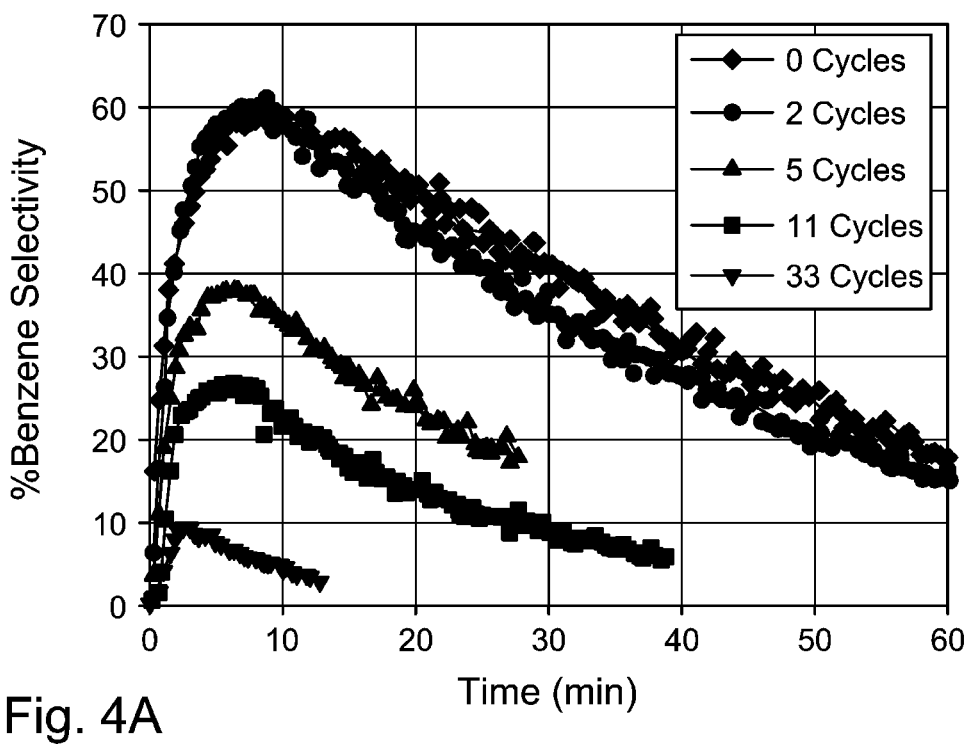
FIGS. 4(a) and 4(b) are graphs of % benzene selectivity (carbon basis) and % methane conversion, respectively, against time for the dehydrocyclization of methane according to the process of Example 2 and using as a catalyst ZSM-5 containing 2.7 wt % molybdenum after the catalyst has undergone a varying number of carburization/oxidative regeneration cycles.
Figure 4B:
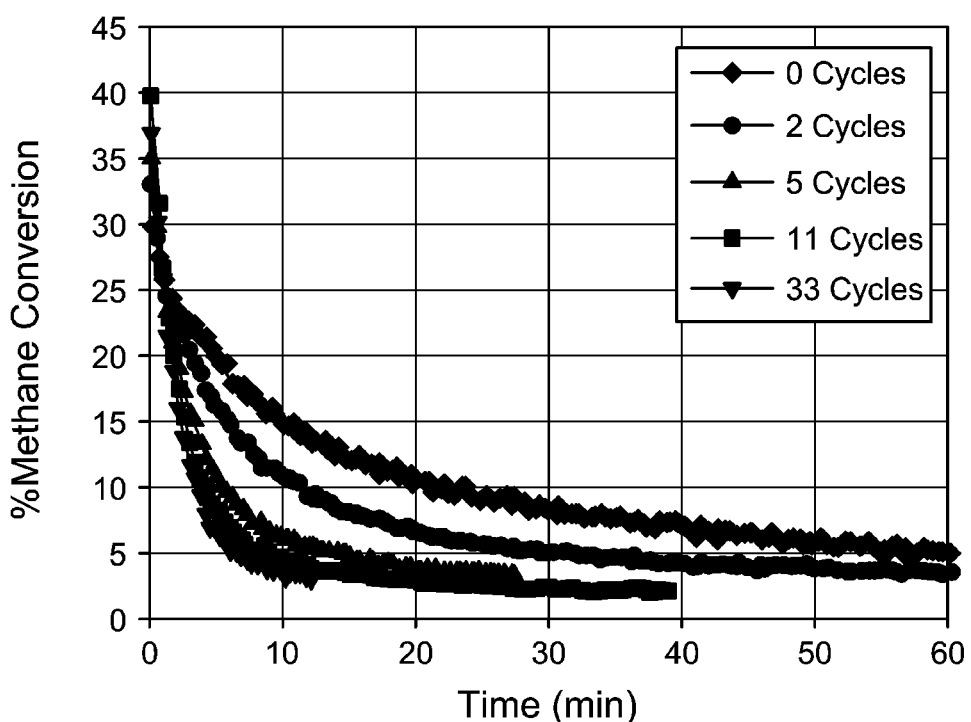

The dehydrocyclization performance of the aged catalysts was measured at 800° C. using 95% CH$_4$—Ar feed at WHSV of 4 hr$^{-1}$ and the results are shown in FIG. 3 and FIGS. 4(a) and 4(b). It is clear from FIG. 3 that with increasing number of carburization-oxidation cycles, the peak benzene yield and overall benzene productivity declines rapidly with cycle number. It is evident from FIGS. 4(a) and 4(b) that, although the initial methane conversion is quite high for aged catalysts, the lifetime of these catalysts is considerably shorter owing to their high coke make (low benzene selectivity).

Figures 5A, 5B:
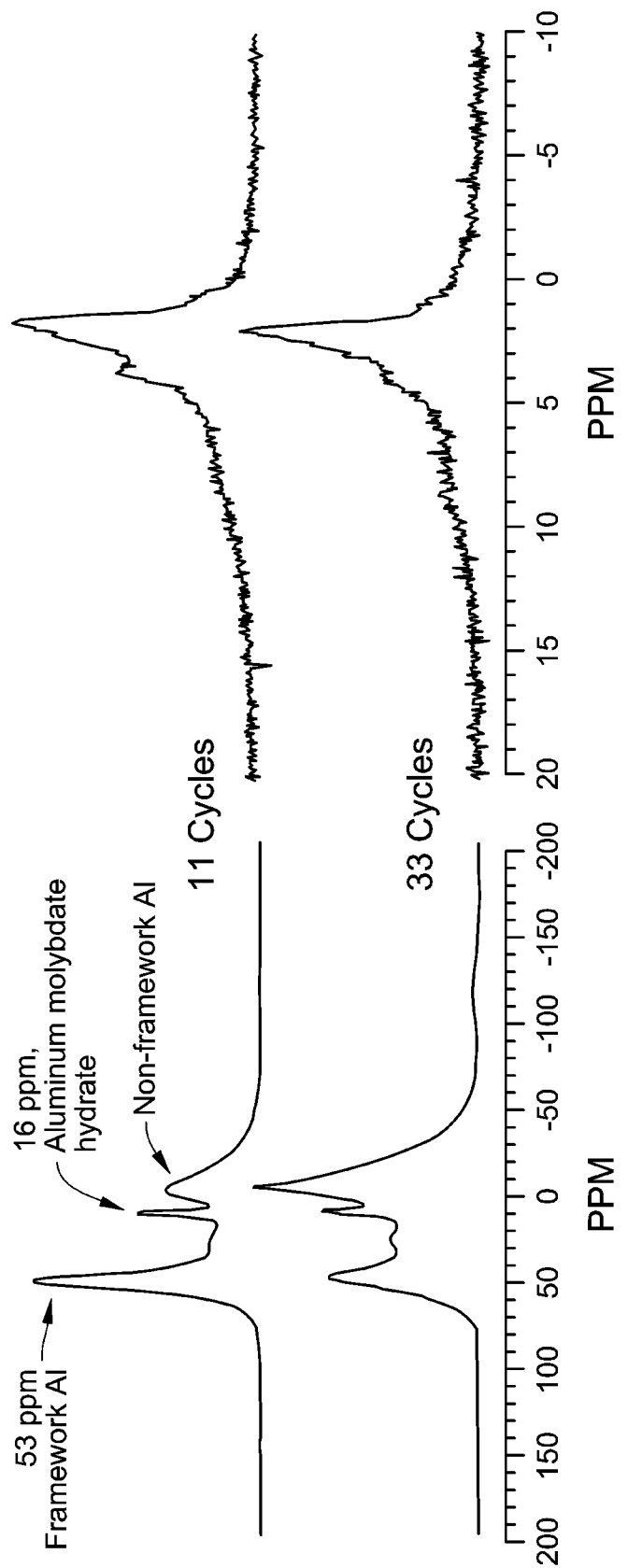
FIGS. 5(a) and 5(b) are $^{27}$Al and $^1$H NMR spectra, respectively, of the 2.7 wt % Mo/ZSM-5 catalyst of Example 2 after the catalyst has undergone a varying number of carburization/oxidative regeneration cycles.

$^{27}$Al and $^{1}$H NMR characterizations for these aged Mo/ZSM-5 catalysts are reported in Table 1 and FIGS. 5(a) and 5(b) and reveal that as the catalyst ages, there is a decrease in Bronsted acidity to essentially zero, a decrease in tetrahedral aluminum, an increase in octahedral aluminum and formation of aluminum molybdate. The fresh catalyst has essentially zero concentration of bulk aluminum molybdate while the catalyst aged to 33 cycles has roughly half of the total Mo associated with Al in the form of aluminum molybdate. The formation of aluminum molybdate results in significant increase in coke make at early TOS due to low benzene selectivity and high initial methane conversion, resulting in rapid catalyst deactivation.

TABLE 1

| Sample | Fresh | 11 cycles | 33 cycles |
|---|---|---|---|
| $^1$H density (mmol/g) | 0.55 | 0.07 | 0.03 |
| Al$_T$ density (mmol/g) | 0.79 | 0.56 | 0.39 |
| Al(OH)MoO$_4$·$x$H$_2$O (mmol/g) | 0.00 | 0.11 | 0.13 |
| BET surface area (m$^2$/g) | 308.1 | 266.1 | 254.7 |
| External surface area (m$^2$/g) | 53.1 | 47.3 | 56.6 |
| Micropore volume (cm$^3$) | 0.12 | 0.11 | 0.09 |
| Pyridine capacity (mmol/g) | 1.44 | 1.27 | 1.13 |

EXAMPLE 3

Figure 6:
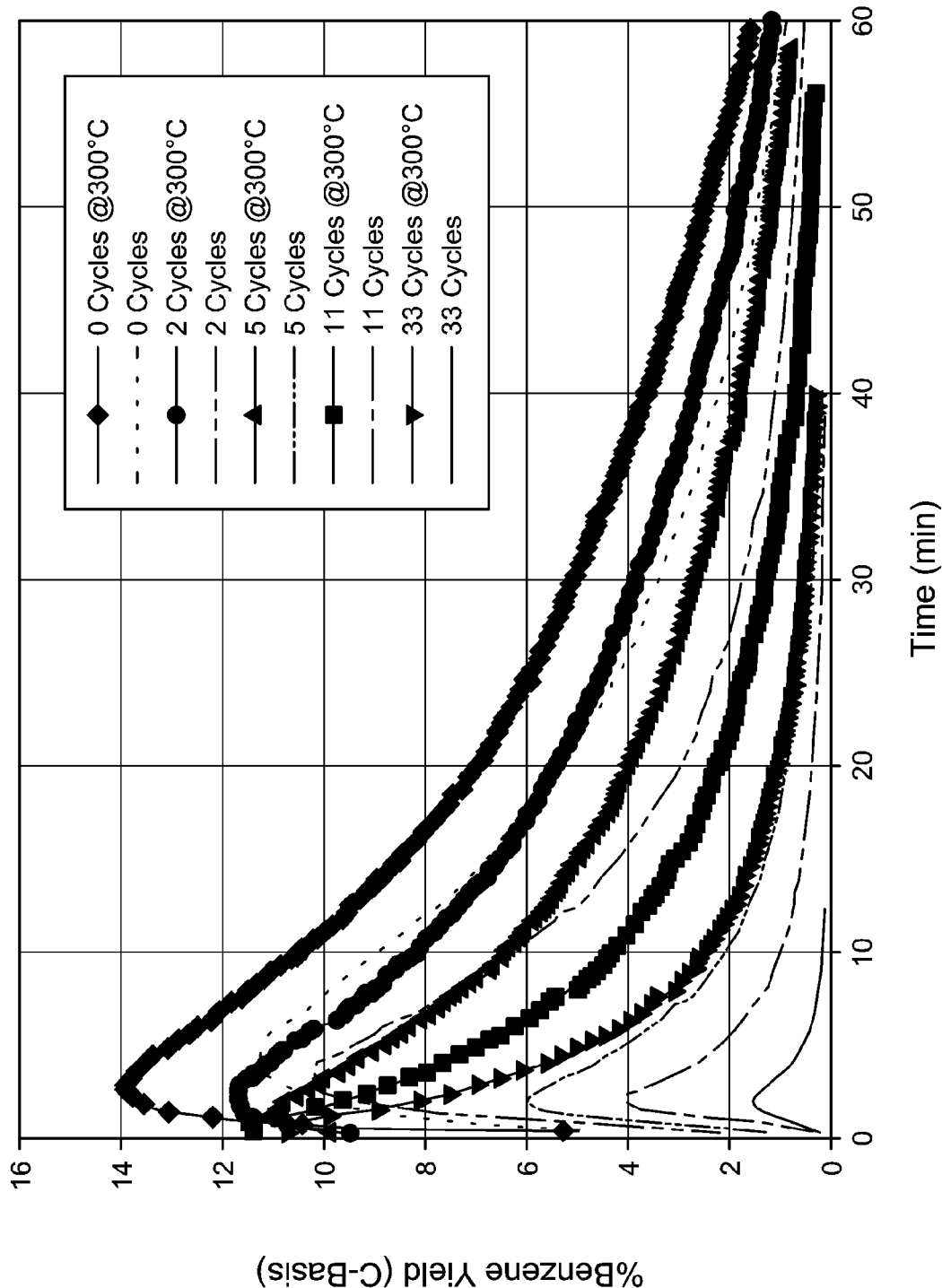
FIG. 6 is a graph of % benzene yield (carbon basis) against time for the dehydrocyclization of methane using the aged 2.7 wt % Mo/ZSM-5 catalysts of Example 2 before and after steaming according to the process of Example 3.
Figures 7A, 7B:
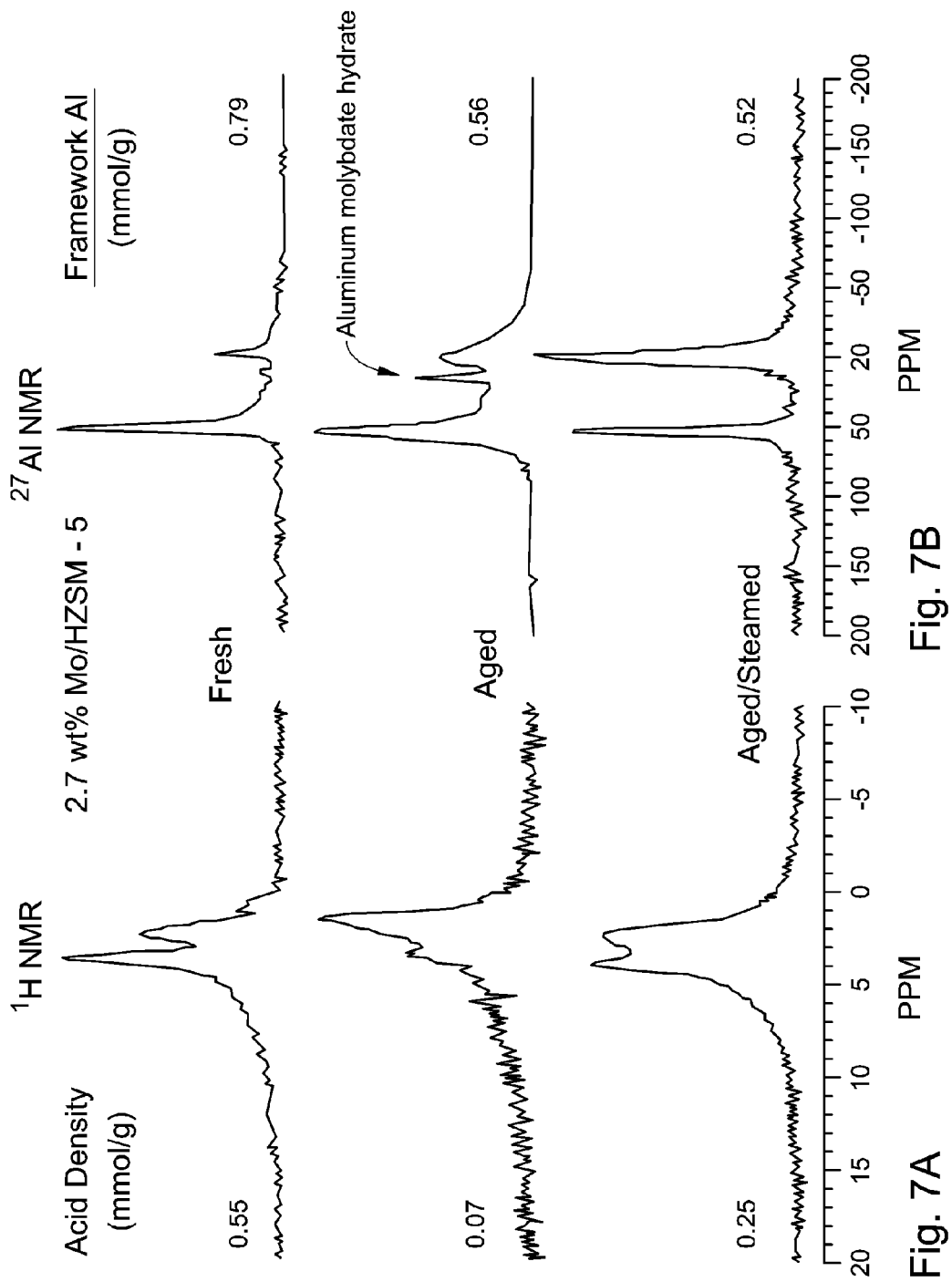
FIGS. 7(a) and 7(b) are $^1$H and $^{27}$Al NMR spectra, respectively, of an aged 2.7 wt % Mo/ZSM-5 catalyst of Example 2 before and after steaming according to the process of Example 3.

The aged 2.7% Mo/ZSM-5 catalysts of Example 2 were steamed for 12 hour at 300° C. in a sealed vessel containing liquid water and the resultant steamed catalysts were subjected to the same dehydrocyclization performance testing as described in Example 2. The results are summarized in FIG. 6, from which it can be seen that the low-temperature steaming resulted in a significant increase in peak benzene yield and overall benzene productivity compared to the non-steamed, aged catalysts. This partial restoration of catalyst activity with low-temperature steaming is consistent with the break-up of aluminum molybdate and its re-dispersion on the partially restored Bronsted acid sites. This is supported by the $^{27}$Al NMR spectrum for post-steamed catalyst shown in FIG. 7(b).

EXAMPLE 4

The procedure of Example 2 was repeated to produce first and second sets of three Mo/ZSM-5 catalysts containing 1.4 wt %, 2.7 wt % and 5.0 wt % respectively of molybdenum. In the first set of catalysts the final calcination temperature was maintained at 500° C., whereas in the second set of catalysts the final calcination temperature was increased to 700° C. The $^1$H and $^{27}$Al NMR spectra of the first set of catalysts are shown in FIGS. 8(a) and 8(b), whereas the spectra of the second set of catalysts are shown in FIGS. 9(a) and 9(b). It is evident from the NMR spectra that aluminum molybdate formation is favored at higher Mo loadings (increasing aluminum molybdate peak with increasing Mo loadings at 700° C.) and higher final calcination temperatures in air (increasing aluminum molybdate peak at 700° C. vs 500° C. calcination).

Figure 10A:
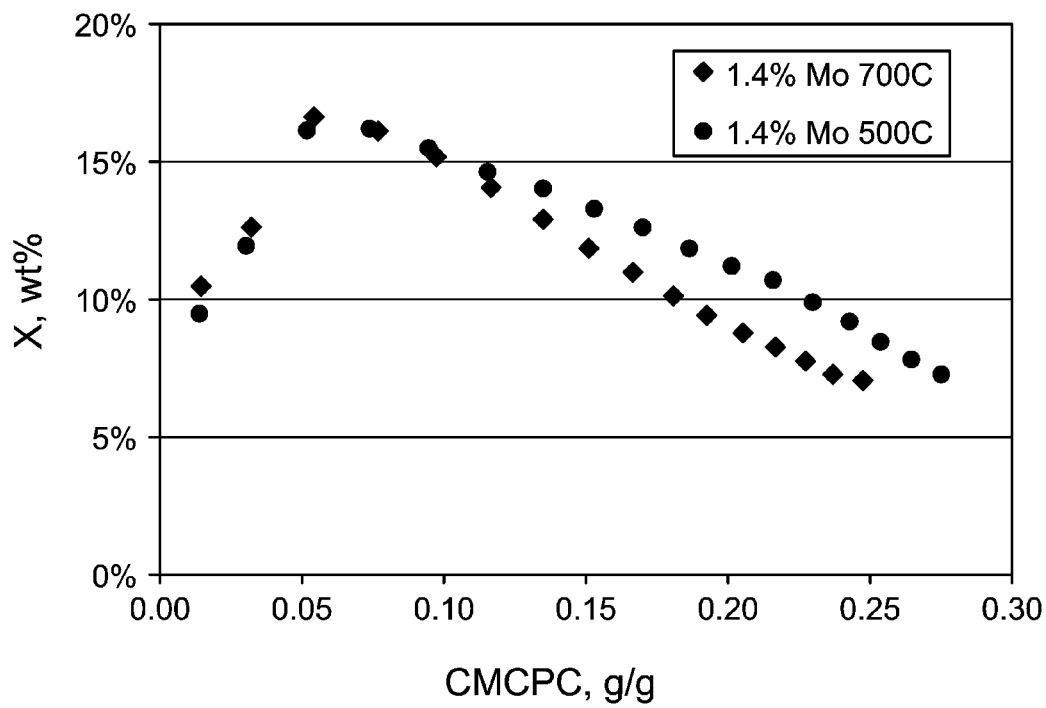
FIGS. 10(a) and 10(b) are graphs comparing the wt % methane conversion (X) and wt % BTN (benzene+toluene+naphthalene) selectivity, respectively, against cumulative grams of methane converted per gram of catalyst (CMCPC)
Figure 10B:
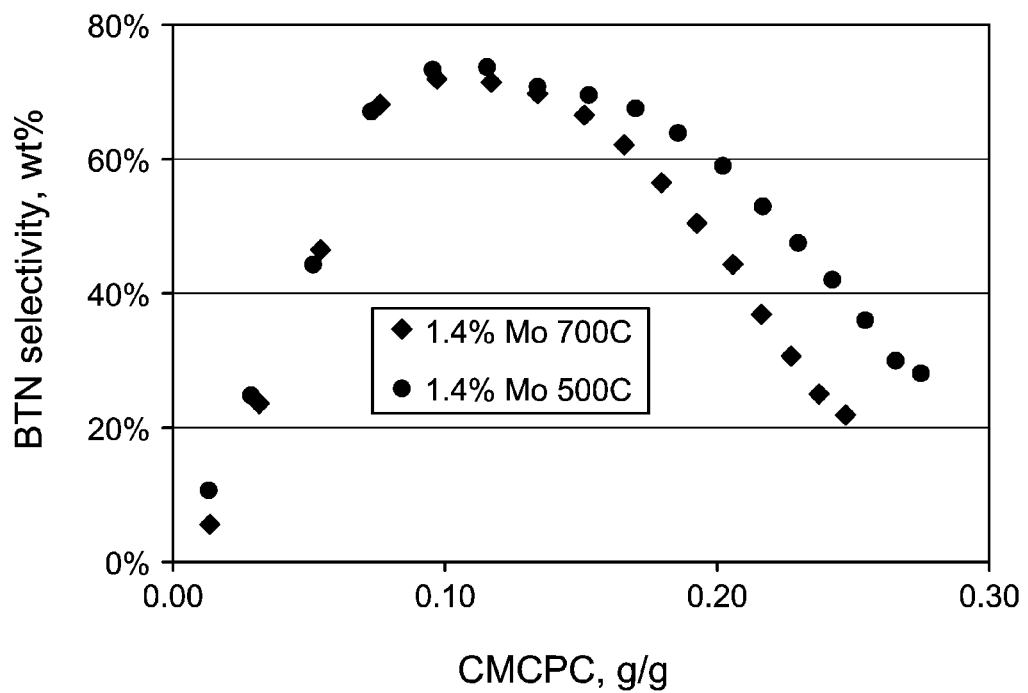

The resultant catalysts were then subjected to the dehydrocyclization performance testing of Example 2. The results are shown in FIGS. 10 to 12, from which the impact of aluminum molybdate formation on catalyst performance is apparent. Since aluminum molybdate formation is more pronounced at 5% Mo loading, the effect of increasing calcination temperature from 500 to 700° C. results in a substantial decrease in benzene selectivity and overall lifetime. However, comparing these results to those for 1.4% Mo loading, it is evident that increasing calcination temperature from 500 to 700° C. did not have as large an impact on performance. This is consistent with the Al NMR results which show significantly lower aluminum molybdate formation for 1.4% vs 5% Mo sample at 700° C.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

EXAMPLE 5

After carburization, a catalyst containing 4.1% Mo/ZSM-5 was taken to complete deactivation by exposing the catalyst to methane containing feed for about 90 minutes. The coked catalyst was distributed in a thin layer in a shallow 6 cm long alumina boat which was then placed in a one inch diameter quartz tube furnace reactor. The tube was purged and the sample dried overnight by flowing dry air while maintaining the temperature of the furnace at 150° C. The sample, which at this time was black in color, was then reacted at 150° C. for 8 hrs with 0.6% ozone at 3500 cc/min. The sample which was now gray in color was allowed to sit overnight at 150° C. in air. A second treatment of 0.6% ozone at 3500 cc/min was performed for 10 hours. The sample changed in color from gray to very light gray in color and again it was allowed to sit overnight at 150° C. in air. A third treatment was done with 0.6% ozone at 3500 cc/min and at 125° C. for 8 hours. The color of the sample did not change significantly from the second treatment. The coked catalyst contained about 10 wt % coke and 80% of coke was removed as a result of the ozone treatment, as measured by temperature-programmed oxidation. The initial coked catalyst sample and a portion of the ozone treated sample were subsequently calcined at 550° C. in air. All three samples (ozone-treated catalyst, ozone-treated then air regenerated catalyst, and air regenerated initial catalyst) were hydrated overnight in 100% RH environment prior to recording $^{27}$Al NMR spectra at 11.7 T, operating at 499.2 MHz for $^1$H and 130.1 MHz for $^{27}$Al. $^{27}$Al NMR spectrum of the ozone treated catalyst indicates that there is no aluminum molybdate present in the catalyst (no peak at chemical shift of ~15 ppm was observed). The advantage of ozone regeneration compared to air regeneration is that it can oxidize coke at temperatures lower than 150° C., hence preventing the formation of aluminum molybdate. When air was used to regenerate the initial catalyst (requiring temperature of 550° C.), formation of aluminum molybdate was observed (appearance of peak at chemical shift of ~15 ppm). Air calcination of the ozone-regenerated catalyst at 550° C. also resulted in aluminum molybdate formation due to exposure to higher temperatures in air.

This ozone regeneration and all air regenerations were done at or near atmospheric pressure but it is recognized that at greater than atmospheric pressure more efficient removal of carbonaceous species may be possible; by more efficient it is meant that less time or lower temperatures may be possible which will reduce the propensity for aluminum molybdate formation.

The invention claimed is:

1. A process for converting methane to higher hydrocarbons including aromatic hydrocarbons, the process comprising contacting a feed comprising methane with a regenerated catalyst in a reaction zone under dehydrocyclization conditions effective to convert said methane to aromatic hydrocarbons including benzene, wherein said regenerated catalyst comprises molybdenum or a compound thereof dispersed on an aluminosilicate zeolite, wherein said aluminosilicate zeolite is selected from a group consisting of ZSM-5, ZSM-11, ZSM-12, ZSM-22, ZSM-23, ZSM-35, ZSM-57 and MCM-22, wherein the amount of aluminum present as aluminum molybdate in said catalyst is less than 2700 ppm by weight; said catalyst characterized by the formation of aluminum molybdate during dehydrocyclization of methane to aromatic hydrocarbons including benzene, wherein the catalyst has been regenerated and prior to regeneration aluminum molybdate was present in the catalyst up to less than 2700 ppm by weight, and wherein said catalyst's exposure during dehydrocyclization and regeneration has been limited to not more than 100 wt ppm molecular oxygen and/or ozone at a temperature not in excess of 500° C. for a cumulative time not greater than 10 hours; wherein the regenerated catalyst, as supplied to the reaction zone, containing less than 270 ppm by weight aluminum present as aluminum molybdate; wherein the catalyst has been regenerated using an ozone-containing gas, said gas optionally further comprising oxygen, at a temperature less than 500° C.

2. The process of claim 1, wherein the process is operated so as to maintain the amount of aluminum present as aluminum molybdate in said catalyst at less than 2700 ppm by weight.

3. The process of claim 1, wherein the amount of molybdenum or said compound thereof in the catalyst is between about 0.1 and about 20% by weight of the catalyst, based on elemental molybdenum, and wherein the aluminosilicate zeolite comprises ZSM-5 that has a silica to alumina mole ratio between about 14 and about 500.

4. The process of claim 1, wherein the process is operated so as to maintain the amount of aluminum present as aluminum molybdate in said catalyst at less than 270 ppm by weight.

5. The process of claim 1, wherein the catalyst exposure has been limited to not more than 10 wt ppm oxygen in an oxygen-containing gas at a temperature not in excess of 550° C. for a cumulative time not greater than 1 hour.

6. The process of claim 1, wherein the catalyst has been regenerated using an ozone-containing gas, said gas optionally further comprising oxygen, at a temperature less than 300° C.

* * * * *